(12) United States Patent
Yeh

(10) Patent No.: US 6,730,088 B2
(45) Date of Patent: May 4, 2004

(54) DEVICE FOR FIXING SPINAL COLUMN UNDER TREATMENT

(76) Inventor: Chung-Chun Yeh, 16, Alley 1, Lane 65, Jen-Ai Road, Section 2, Taipei (TW)

(*) Notice: Subject to any disclaimer, the term of this patent is extended or adjusted under 35 U.S.C. 154(b) by 70 days.

(21) Appl. No.: 10/145,743

(22) Filed: May 16, 2002

(65) Prior Publication Data

US 2003/0045877 A1 Mar. 6, 2003

(30) Foreign Application Priority Data

Aug. 29, 2001 (TW) ......................................... 90214820 U

(51) Int. Cl.⁷ .............................................. A61B 17/70
(52) U.S. Cl. ..................................... 606/61; 623/17.11
(58) Field of Search .................. 606/60, 61; 623/16.11, 623/17.11, 17.15, 17.16

(56) References Cited

U.S. PATENT DOCUMENTS

| | | | | |
|---|---|---|---|---|
| 4,759,766 A | * | 7/1988 | Buettner-Janz et al. | 623/17.15 |
| 5,480,442 A | * | 1/1996 | Bertagnoli | 623/17.14 |
| 5,534,029 A | * | 7/1996 | Shima | 623/17.15 |

\* cited by examiner

*Primary Examiner*—Kevin Shaver
*Assistant Examiner*—Michael B. Priddy
(74) *Attorney, Agent, or Firm*—Bacon & Thomas, PLLC

(57) ABSTRACT

A spinal column fixation device includes a support member, a top seat fastened at the top end with the support member, and a bottom seat fastened at the bottom end with the support member. The top seat and the support member are fastened by an angle adjusting mechanism such that the angle between the top seat and the support member is adjustable. The bottom seat and the support member are fastened by an angle adjusting mechanism such that the angle between the bottom seat and the support member is adjustable.

5 Claims, 6 Drawing Sheets

DEVICE FOR FIXING SPINAL COLUMN UNDER TREATMENT

FIELD OF THE INVENTION

The present invention relates generally to a device for fixing a deformed or diseased spine, and more particularly to a spine fixation device adjustable in angle in relation to curvature of the spine.

BACKGROUND OF THE INVENTION

As illustrated in FIGS. 1a–1c, the conventional backbone fixation device can not be adjusted in angle in relation to curvature of the backbone. In light of this deficiency, the conventional backbone fixation device is not adapted for use in the intervertebral fixation surgery. If the conventional backbone fixation device is used forcibly to fix the spinal segments under treatment, it is very likely that an improper fixation is resulted from such forcible use of the device.

SUMMARY OF THE INVENTION

The primary objective of the present invention is to provide a spinal column fixation device which is adjustable in angle.

It is another objective of the present invention to provide a spinal column fixation device which has an angle adjusting mechanism.

It is still another objective of the present invention to provide a spinal column fixation device which has an angle adjusting mechanism and a height adjusting mechanism.

The spinal column fixation device of the present invention comprises:

a support member;

a top seat joined with a top end of said support member; and a bottom seat joined with a bottom end of said support member;

wherein said top seat and/or said bottom seat are joined to said support member with an angle adjusting mechanism, so that said top seat and/or said bottom seat can be fixedly joined with said support member in various angles formed between said support member and said top seat and/or said bottom seat.

Preferably, said support member has a height adjusting mechanism.

Preferably, said height adjusting mechanism is formed of an upper support body, a lower support body, and an adjustment ring; wherein said lower support body is fastened with said adjustment ring, and said upper support body is threadably received in said adjustment ring, so as to attain the function of height adjustment.

Preferably, said top seat and said bottom seat are independently joined to said support member with an angle adjusting mechanism.

Preferably, said angle adjusting mechanism comprises a serrated recessed curved surface and a serrated protruded curved surface, provided that one is formed on said support member and another one is formed on said top seat or said bottom seat; and a pivotally fastening means, wherein said pivotally fastening means fastens said top seat or said bottom seat to said support member with said serrated recessed curved surface and said serrated protruded curved surface being engaged with each other.

DETAILED DESCRIPTION OF THE INVENTION

Figure 1A:
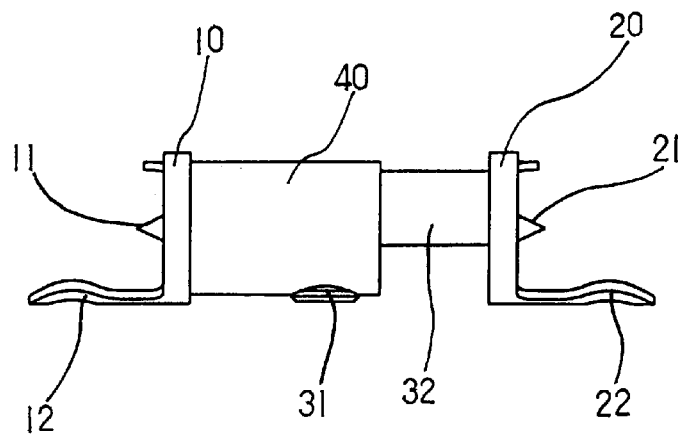
FIGS. 1a–1c are schematic views of a backbone fixation device of the prior art.
Figure 1B:
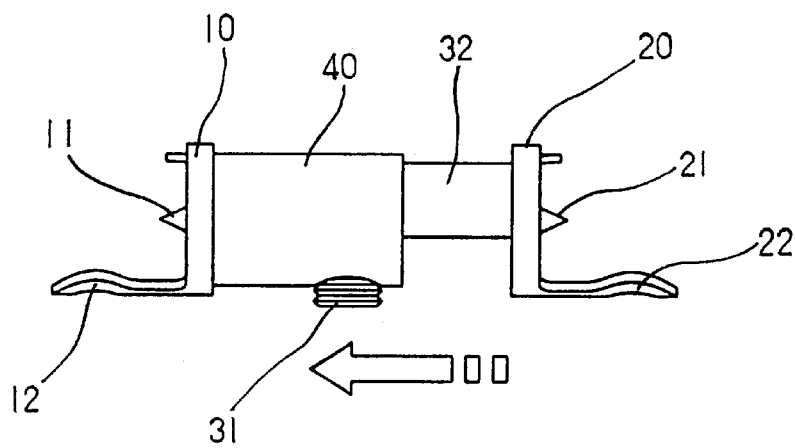
Figure 1C:
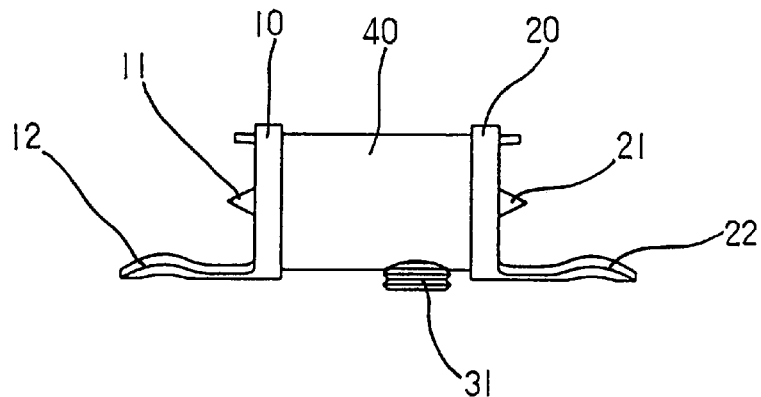

Before describing the present invention, it is necessary to describe the prior art device. As illustrated in FIGS. 1a–1c, the prior art device comprises a fixation seat 10 which is provided with fixation teeth 11 and a fixation side piece 12, an upper fixation seat 20 which is provided with fixation teeth 21 and a fixation side piece 22, a fixation screw 31, a height adjusting member 32, and a support member 40. FIG. 1a shows a schematic view of the height adjusting member which is adjusted to a higher state. FIG. 1b shows a schematic view of the screw 31 which is unfastened to facilitate the inserting of the height adjusting member 32 into the support member 40, as shown in FIG. 1c.

Figure 2:
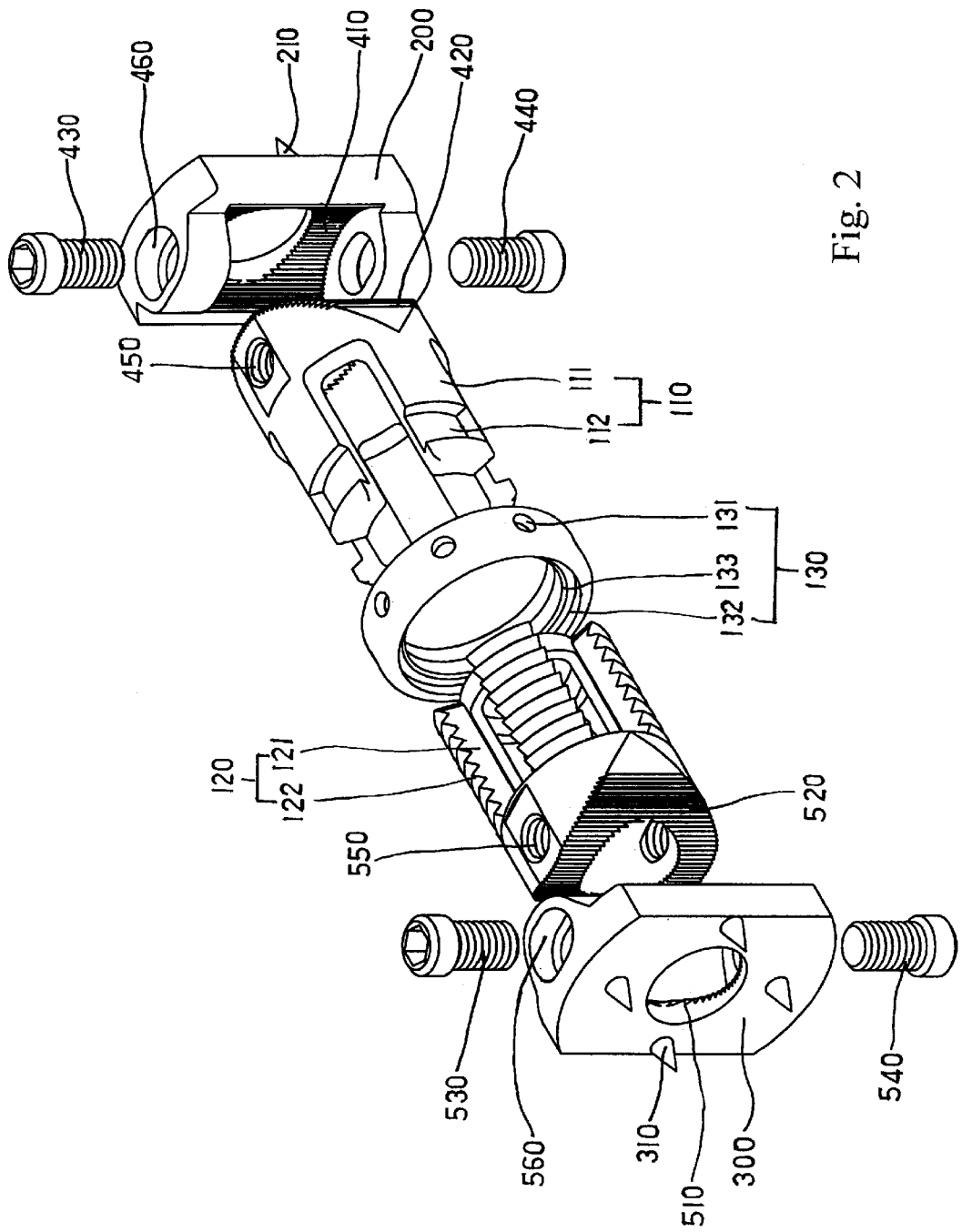
FIG. 2 shows an exploded view of a preferred embodiment of the present invention.
Figure 3:
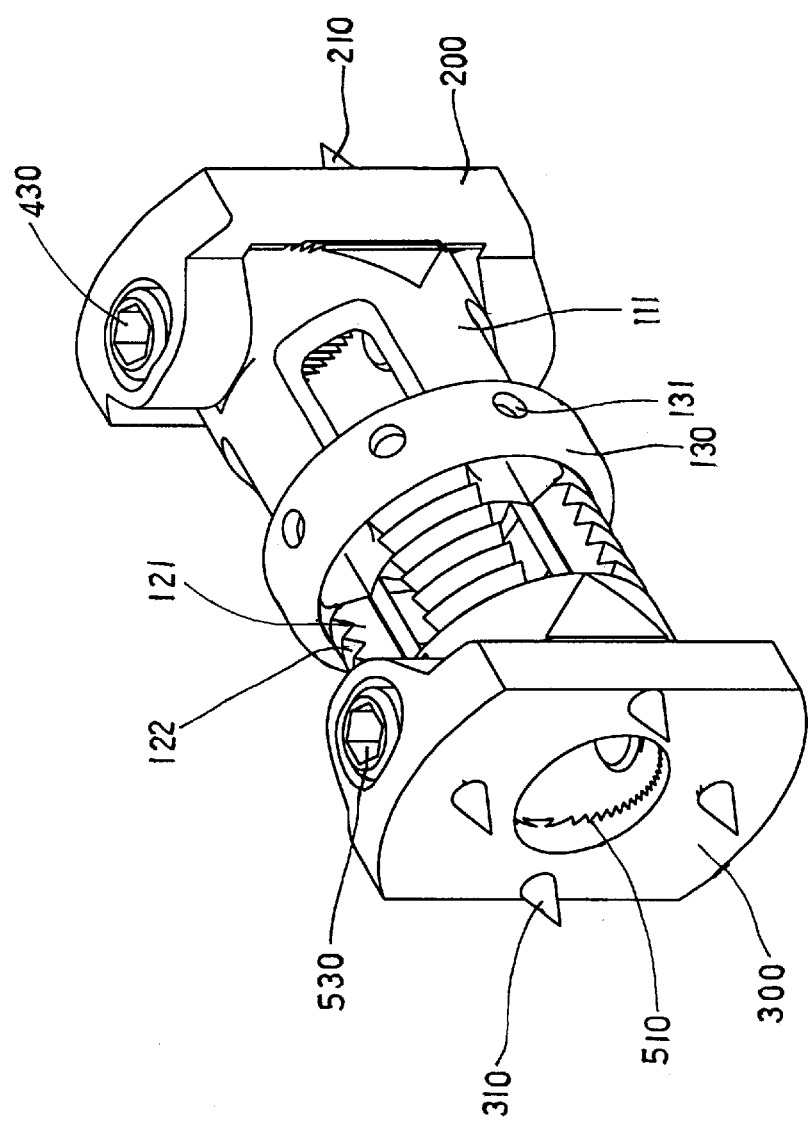
FIG. 3 shows a perspective view of the preferred embodiment of the present invention in combination.
Figure 4A:
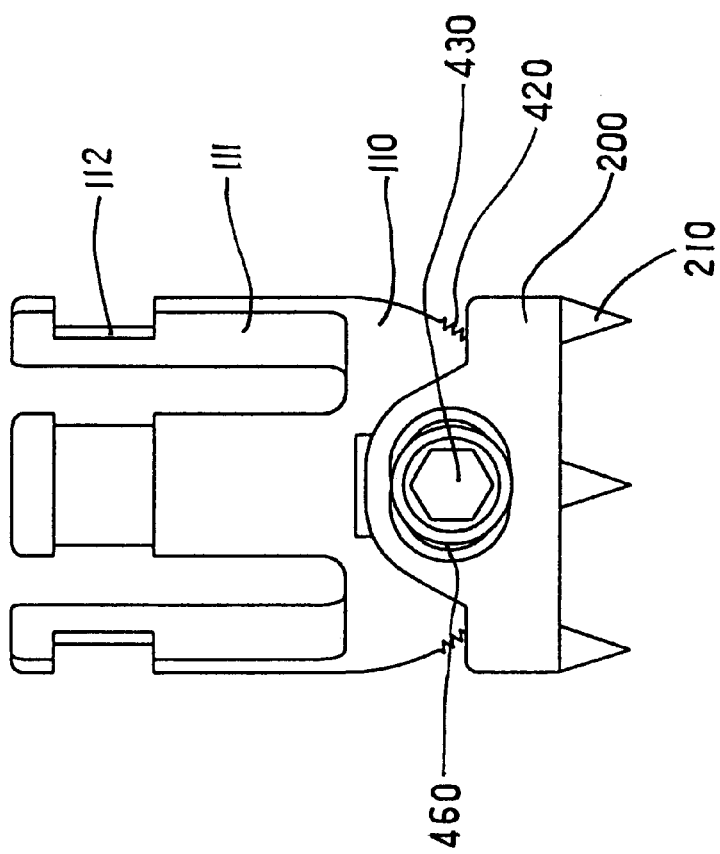
FIGS. 4a, 4b, 5a and 5b are schematic views of the angle adjusting mechanism of the preferred embodiment of the present invention.
Figure 4B:
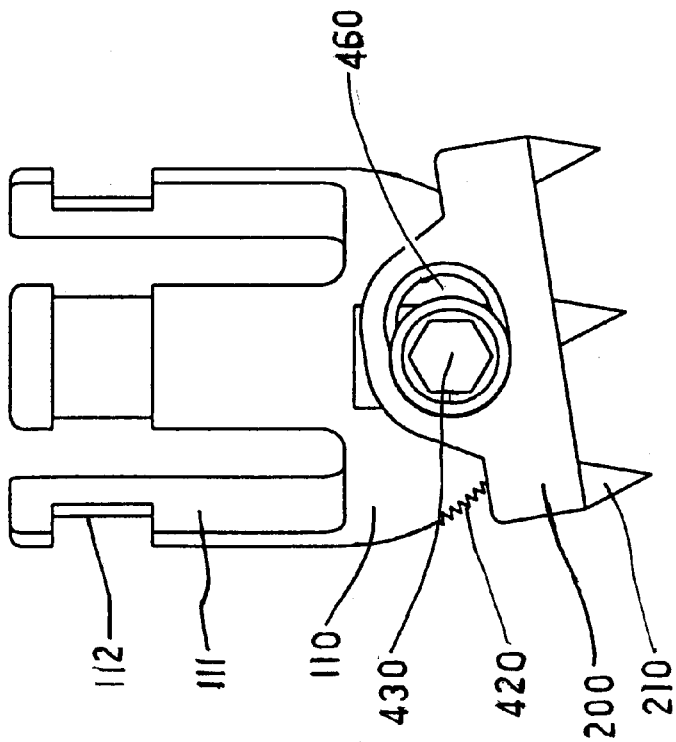
Figure 5A:
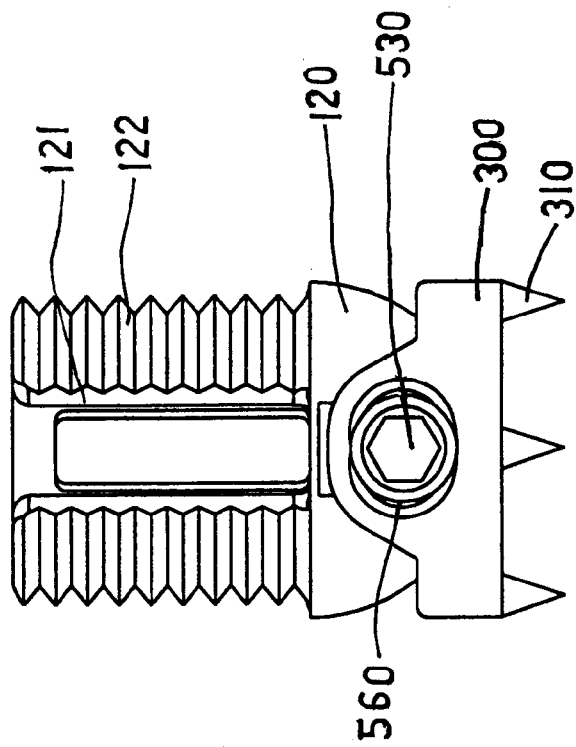
Figure 5B:
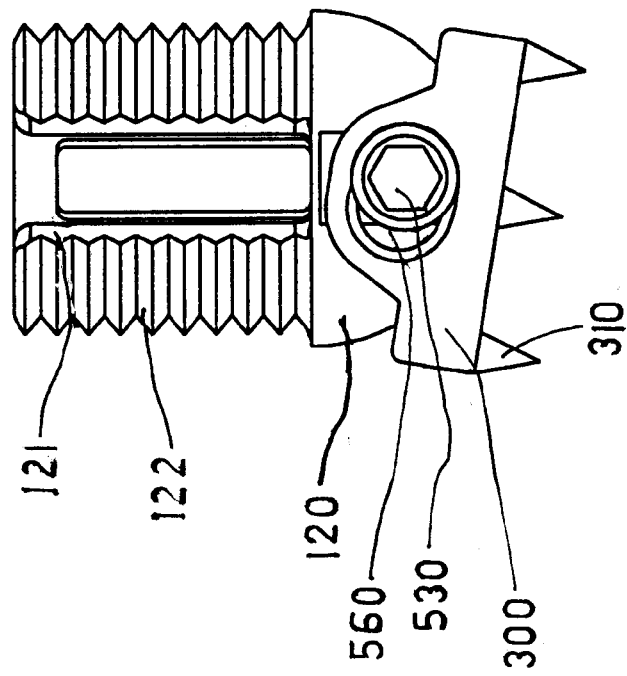

As shown in FIGS. 2 and 3, the present invention comprises a lower support body 110 which is provided with lower support legs 111 and fixation recesses 112; an upper support body 120 which is provided with upper support legs 121 and threaded teeth 122 on the support legs 121; an adjustment ring 130 which is provided with tool holes 131, threaded teeth 132, and a rib 133; a bottom seat 200 provided with fixation teeth 210; a top seat 300 provided with fixation teeth 310. An angle adjusting mechanism includes a serrated recessed curved surface 410 (510), a serrated protruded curved surface 420 (520), two fixation screws 430 and 440 (530, 540), two fixation threaded holes 450 (550), and two fixation holes 460 (560). The recessed curved surface 410, the protruded curved surface 420, the fixation screws 430 and 440, the fixation threaded holes 450 and the fixation holes 460 of the lower angle adjusting mechanism are assembled in two different angles as shown in FIGS. 4a and 4b, respectively. The recessed curved surface 510, the protruded curved surface 520, the fixation screws 530 and 540, the fixation threaded holes 550 and the fixation holes 560 of the upper angle adjusting mechanism are assembled in two different angles as shown in FIGS. 5a and 5b, respectively. For the height adjusting mechanism which is formed of the upper support body 120, the lower support body 110 and the adjustment ring 130, please refer to FIGS. 6a and 6b.

FIG. 4a shows that the bottom seat 200 and the lower support body 110 are joined together in normal direction such that the fixation screw 430 is located at the center of the fixation hole 460. The reference numerals of 110, 111, 112, 200, 210, 420, 430, and 460 are same in definition as those of FIG. 2.

FIG. 4b shows that the bottom seat 200 and lower support body 110 are joined together slantingly such that the fixation screw 430 is located at one side of the fixation hole 460. The reference numerals of 110, 111, 112, 200, 210, 420, 430, and 460 are same in definition as those of FIG. 2.

FIG. 5a shows that the upper seat 300 and the upper support body 120 are joined together in normal direction such that the fixation screw 530 is located at the center of the fixation hole 560. The reference numerals of 120, 121, 122, 300, 310, 530, and 560 are same in definition as those of FIG. 2.

FIG. 5b shows that the upper seat 200 and the upper support body 120 are joined together slantingly such that the fixation screw 530 is located at one side of the fixation hole 560. The reference numerals of 120, 121, 122, 300, 310, 530, and 560 are same in definition as those of FIG. 2.

Figure 6A:
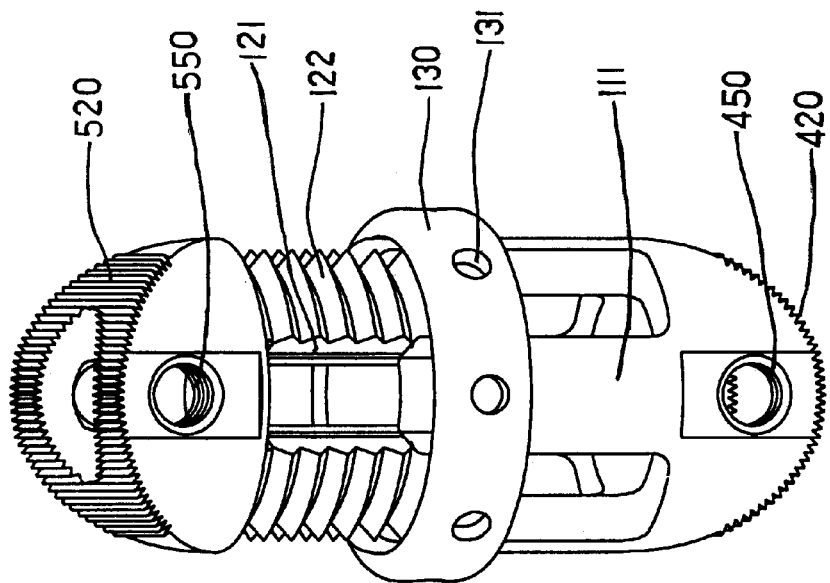
FIGS. 6a and 6b are schematic views of the height adjusting mechanism of the preferred embodiment of the present invention.
Figure 6B:
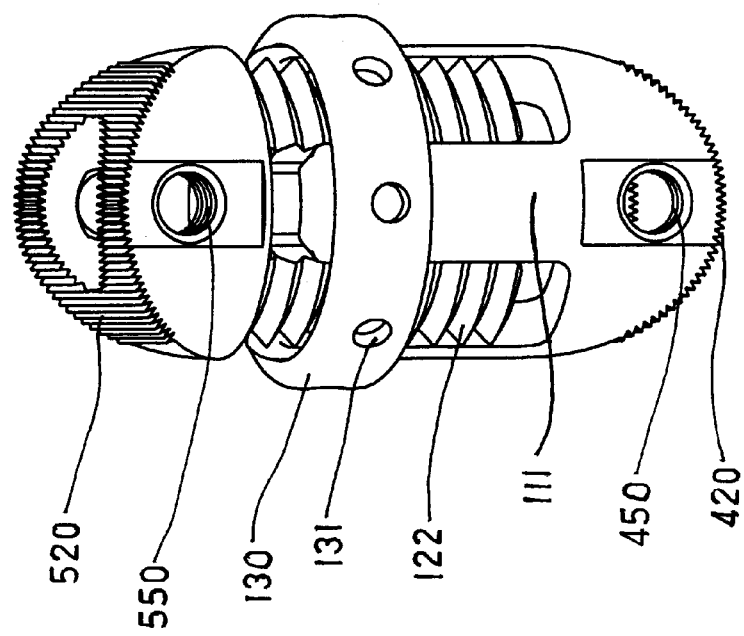

FIG. 6a shows that each upper support leg 121 is fitted between two lower support legs 111 of the lower support body. The adjustment ring 130 is fitted over the lower support legs 111 such that the rib 133 (shown in FIG. 2) is received in the fixation recess 112 (shown in FIG. 2) on the lower support legs 111, thereby resulting in the union of the lower support body and the adjustment ring. The threaded teeth 132 (shown in FIG. 2) of the adjustment ring 130 is engaged with the teeth 122 of the upper support body to enable the union of the upper support body and the adjustment ring. The reference numerals of 111, 121, 122, 130, 131, 420, 450, 520, and 550 are similar in definition to those of FIG. 2. As shown in FIG. 6b, the threaded teeth 132 (shown in FIG. 2) of the adjustment ring 130 and the teeth 122 (shown in FIG. 2) of the upper support body are different in engagement position, so as to form the support member of different height. The adjustment of height of the support member is attained by a tool which is inserted into the tool holes 131 to rotate the adjustment ring 130.

The embodiment of the present invention is nonrestrictive. Accordingly, the present invention may be embodied in other specific forms. For example, the shape and the structure of the top seat 300 are not restrictive and may be similar to the fixation seat of the prior art fixation device, as shown by reference numerals of 10 and 20 of FIG. 1a.

The shape and the structure of the bottom seat 200 are not restrictive and may be similar to the fixation seat of the conventional fixation device, as indicated by 10 and 20 of FIG. 1a.

The shape of the support member of the present invention is not restrictive, provided that the fastening of the top seat and/or the bottom seat to the support member is provided with the angle adjusting mechanism, which may be a gear-type angle adjusting mechanism, or the curved surface threadedly fastening type angle adjusting mechanism as shown in FIG. 2.

The fastening of the support member and the top seat, and the fastening of the support member and the bottom seat, preferably, both are provided with the angle adjusting mechanism. When the support member and the top seat (or the support member and the bottom seat) are joined together without the angle adjusting mechanism, the top seat (or the bottom seat) is formed integrally with the support member, such as the reference numerals of 10 and 40 of FIG. 1a. When the support member and the top seat (or support member and bottom seat) are joined together along with the angle adjusting mechanism, the angle adjusting mechanism is located in its entirety on the support member or the top seat (or bottom seat); partially located on the support member and partially located on the top seat (or bottom seat); or partially located on the support member, partially located on the top seat (or bottom seat), and partially for fixedly connecting the support member and the top seat (or bottom seat).

The support member may not have or may have a height adjusting mechanism which is the same as the conventional height adjusting mechanism as shown in FIG. 1a.

What is claimed is:

1. A spinal column fixing device comprising:

a support member;

a top seat joined with a top end of said support member;

a bottom seat joined with a bottom end of said support member;

wherein said top seat or said bottom seat are joined to said support member with an angle adjusting mechanism, so that said top seat or said bottom seat can be fixedly joined with said support member in various angles formed between said support member and said top seat or said bottom seat;

said angle adjusting mechanism comprises a serrated recessed curved surface and a serrated protruded curved surface, provided that one is formed on said support member and another one is formed on said top seat or said bottom seat; and a pivotally fastening means, wherein said pivotally fastening means fastens said top seat or said bottom seat to said support member with said serrated recessed curved surface and said serrated protruded curved surface being engaged with each other.

2. The device as defined in claim 1, wherein said support member has a height adjusting mechanism.

3. The device as defined in claim 2, wherein said height adjusting mechanism is formed of an upper support body, a lower support body, and an adjustment ring; wherein said lower support body is fastened with said adjustment ring, and said upper support body is threadably received in said adjustment ring, so as to attain the function of height adjustment.

4. The device as defined in claim 2, wherein said height adjusting mechanism is formed of an upper support body, a lower support body, and an adjustment ring; wherein said upper support body is fastened with said adjustment ring, and said upper support body is threadably received in said adjustment ring, so as to attain the function of height adjustment.

5. The device as defined in claim 1, wherein said top seat and said bottom seat are independently joined to said support member with said angle adjusting mechanism.

* * * * *